United States Patent [19]

Espenscheid et al.

[11] 4,395,902

[45] Aug. 2, 1983

[54] METHOD AND APPARATUS FOR DETERMINING PHASE BEHAVIOR OF OIL/GAS MIXTURES AT HIGH PRESSURES AND TEMPERATURES

[75] Inventors: Wilton F. Espenscheid, DeSoto; Richard E. Aikin, Grapevine, both of Tex.

[73] Assignee: Mobil Oil Corporation, New York, N.Y.

[21] Appl. No.: 307,554

[22] Filed: Oct. 1, 1981

[51] Int. Cl.³ .............................................. G01N 7/14
[52] U.S. Cl. ........................................ 73/19; 73/61 R
[58] Field of Search ......................... 73/19, 61 R, 153

[56] References Cited

U.S. PATENT DOCUMENTS 3,911,256 10/1975 Jones .................................. 73/61 R

FOREIGN PATENT DOCUMENTS 7805679 11/1978 Netherlands ............................ 73/19

Primary Examiner—Stephen A. Kreitman
Attorney, Agent, or Firm—Charles A. Huggett; James F. Powers, Jr.; Lawrence O. Miller

[57] ABSTRACT

A method and apparatus for determining the phase behavior of gas/oil mixtures at preselected controlled high temperatures and high pressures wherein a stream of oil and gas under controlled conditions of volume rate and pressure are separately introduced into a mixing chamber and then into a separator wherein the liquid oil phase separates by gravity into the bottom of the separator and the gas phase migrates by gravity to the top of the separator. The gas phase of the separator is in fluid communication with a pressure control system. Samples of oil and gas are separately withdrawn from the separator after thermo-dynamic equilibrium is reached in the mixing chamber and each sample is analyzed to measure the gas/oil ratio.

23 Claims, 1 Drawing Figure

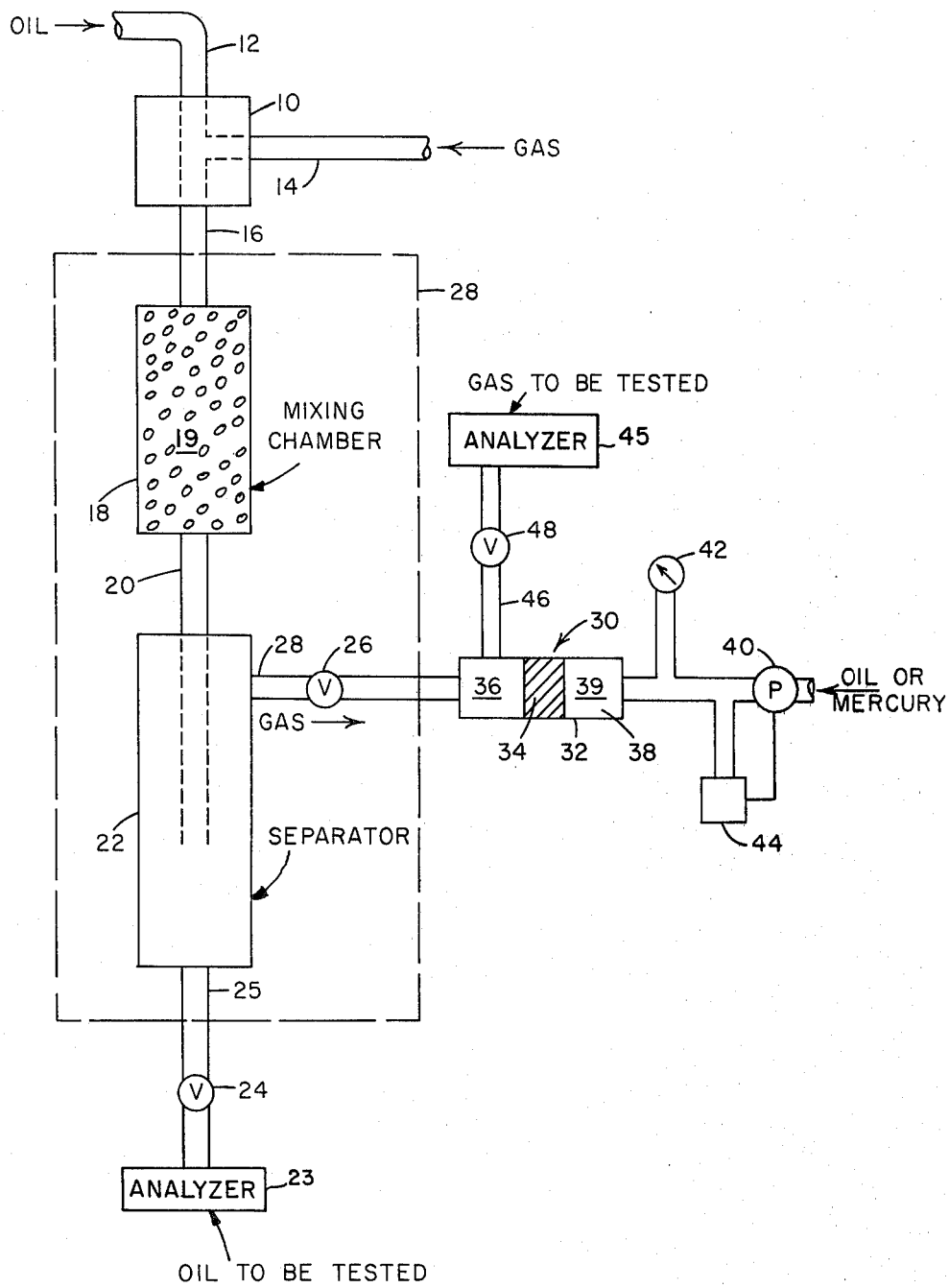

METHOD AND APPARATUS FOR DETERMINING PHASE BEHAVIOR OF OIL/GAS MIXTURES AT HIGH PRESSURES AND TEMPERATURES

BACKGROUND OF THE INVENTION

1. Field of the Invention

This invention relates to a method and apparatus for determining the phase behavior of oil/gas mixtures at controlled high pressures and temperatures.

2. Description of the Prior Art

Many procedures associated with the production of oil and gas require detailed knowledge of the phase behavior of gas/oil mixtures at high pressures and temperatures. Contact between an oil and a gas at elevated pressures and temperatures often produces an oil phase cut with gas, and a gas phase containing often high concentrations of oil. The purpose of phase-behavior studies is to determine quantitatively the composition and volume of each phase at various pressures and temperatures. Such data is fundamental to the continuous circulation of corrosion inhibitors in deep high-pressure sour-gas wells, or to enhance oil recovery by $CO_2$-flooding. In the case of continuous circulation of corrosion inhibitors, this may involve measurements performed at pressures to 20,000 psig. and temperatures to 500° F.

The present accepted technique for performing such studies consists of charging a small quantity of oil (say, 10-15 gm) into a high-pressure cell, and following this with a charge of gas (which may equal 150 liters of methane, carbon dioxide, hydrogen sulfide, etc., or mixtures thereof). The whole cell is then brought to the desired pressure and temperature. Data is taken by venting small quantities of the gas phase through a trap, and subsequently measuring the volume of gas vented and weighing the liquid (oil) collected. This process is conducted while the cell and its contents are nearly maintained at constant pressure and temperature.

The previously discussed techniques suffer several serious drawbacks:

(1) Since the cell that contains the oil/gas mixture is also brought to high pressure and temperature, strength of materials becomes an overriding safety consideration. Also, the presence of corrosive $H_2S$ and $CO_2$ gases often dictates the use of expensive alloys to prevent $H_2/H_2S$ embrittlement. Massive, thermally controlled cells fabricated from $30–$50/lb. alloys (Hastaloy C-276, MP35N, etc.) are expensive, require extremely long delivery times, and are not generally available on a contract basis.

(2) In conducting studies at high pressures and temperatures, the volume of the liquid phase is often reduced to less than 10% of the original charge. The liquid phase composition can only be estimated from the gas phase composition, and the volume of the liquid phase cannot be measured directly because of its small volume.

SUMMARY OF THE INVENTION

In accordance with the present invention, there is provided an apparatus for determining the phase behavior of oil/gas mixture at controlled high temperatures and pressures comprising a mixing chamber and means for supplying separate streams of oil and gas to said mixing chamber under controlled conditions of volume per unit time and pressure. A separator is positioned below said mixing chamber in fluid communication therewith wherein the mixed oil and gas effluent from the mixing chamber separate by gravity with the oil phase collecting in the bottom of the separator and the gas phase migrating to the top of the separator. Means are provided for surrounding the mixing chamber and separator within a medium heated to a controlled, constant, elevated temperature such as an oven or a heated sand bath. Means are also provided for controlling the absolute pressure of the gas within the separator in addition to means for withdrawing gas samples from the upper portion of the separator and oil samples from the lower portion of the separator. Means are provided for measuring the amount of gas contained in the sample of oil and the amount of oil contained in the sample of gas.

In accordance with another aspect of the invention, there is provided a method for determining the phase behavior of an oil/gas mixture at a predetermined temperature and pressure. The method comprises separately feeding a flowing stream of oil and gas into a mixing chamber under controlled conditions of volume per unit time and pressure. The effluent of mixed oil and gas from the mixing chamber is then passed into a separator wherein the oil and gas separate by gravity with the oil collecting in the bottom of the separator and the gas migrating to the top of the separator. The mixing chamber and the separator are surrounded by a medium heated to a controlled, constant, elevated temperature. Gas is withdrawn from the upper portion of the separator and is in fluid communication with a pressure controlling means to maintain the absolute pressure of the gas within the separated valve at a predetermined volume. Samples of gas are withdrawn from the upper portion of the separator and analyzed to determine the content of oil in said gas. Samples of oil are withdrawn from the lower portion of the separator and analyzed to determine the content of gas in the oil. Samples of oil and gas are withdrawn when thermo-dynamic equilibrium is reached in the mixing chamber.

BRIEF DESCRIPTION OF THE DRAWING

The attached drawing is a somewhat schematic illustration of the system used in this invention for measuring the phase behavior of oil and gas mixtures at high pressures and temperatures.

DESCRIPTION OF SPECIFIC EMBODIMENTS

The present invention relates to a method and apparatus for determining the phase behavior of oil and gas mixtures at high pressures and temperatures.

In the drawing oil having a boiling range between 300° F. to 1500° F. and gas such as methane, hydrogen sulfide, carbon dioxide, or mixtures thereof are separately pumped under controlled pressure and volume rate into a blending "tee" 10 with the oil entering through line 12 and the gas entering through line 14. The oil rate is from about 0.5 cc/hr. to 50 cc/hr., and preferably 5 to 15 cc/hr. The gas rate is from about 50 to 300 liters/hr. and preferably 100 to 200 liters/hr. at standard temperature and pressure. The combined oil and gas stream then passes through line 16 and into a mixing chamber 18 which may consist of a short (e.g., 6") section of heavy wall tubing filled with inert chips of silica 19 or other suitable material or consist of a coil of small-diameter high-pressure tubing. The mixture of oil and gas then passes through line 20 into a high-pressure gas-liquid separator 22 wherein the liquid oil phase separates into the bottom of the separator by gravity and the gas phase rises to the top of the separator. It is preferred that line 20 extend substantially into separator 22 as illustrated in the drawing so that the oil/gas mixture enters the separator intermediate the lower portion of the separator and the upper portion thereof for more effective separation. Means are provided to withdraw samples of oil to be analyzed from the separator 22 through valve 24 via line 25. The separator 22 may consist of a small high-pressure "bomb," or may be fabricated simply from heavy-walled tubing.

The mixing chambers 18 and separator 22 are placed in a suitable controlled temperature environment indicated by dashed lines 28 such as an oven, a heated sand bath, or other suitable means. The bath temperature is controlled from at least about 100° F. to about 600° F., and preferably from 300° F. to 450° F. As a result, only a few small light-weight components are subjected to high temperatures, and the small diameter involved allows fabrication of the mixing chamber 18 and separator 22 from materials having wall thicknesses less than $\frac{1}{4}''$ (e.g., 9/16" O.D.×5/16" I.D., 316 SS. capable of withstanding an internal working pressure of at least 20,000 psi with a suitable factor of safety). The size of the mixing chamber 18 is adjusted so that the residence time of the oil and gas in the chamber is sufficient to reach a level of thermo-dynamic equilibrium.

The gas phase passes from the top of the high-pressure separator 22 through valve 26 via line 28 and into a pressure control system 30. The pressure control system 30 comprises a cylinder 32 divided into two chambers by a piston 34 that moves longitudinally in sealing engagement with the internal walls of the cylinder. The left chamber 36 of cylinder 32 is in fluid communication with the gas phase from the separator 22 which is maintained at a constant, controlled and predetermined high test pressure by piston 34. The high test pressure is maintained on the other side of piston 34 by hydraulic pressure of a fluid 38 such as oil, mercury, or air contained in the right chamber 39 of the cylinder 32. The hydraulic pressure of the fluid 38 is maintained by means of a constant displacement pump 40 or other suitable means such as a manually operated hydraulic press. This pressure which is indicated by gauge 42 may be controlled manually or, more preferred, by sensing the pressure with a sensing element 44 such as a pressure transducer in fluid communication with the interior of chamber 39 which generates a signal representative of the pressure in chamber 39 and controls the pressure electronically by feeding the signal from the sensing element to pump 40. The pressure control system controls the absolute pressure of the gas contained in separator 22 within the range of 2,000 to 20,000 psi, and preferably 8,000 to 15,000 psi. Means are provided to withdraw samples of gas to be analyzed from chamber 36 through valve 48 via line 46.

Gas and oil samples are withdrawn from the apparatus for analysis when thermo-dynamic equilibrium is reached in the mixing chamber and at a time period wherein sufficient amounts of oil and gas are obtainable based upon the size of the sample required for the gas/oil ratio analyzer. At this point, a sample of oil is withdrawn from the bottom separator 22 through valve 24 via line 25 and sent to an analyzer 23 to measure the content of the gas in the oil. A sample of gas is withdrawn from chamber 36 of the pressure control system 30 through valve 48 via line 46 and sent to an analyzer 45 to measure the content of the oil in the gas phase. By periodically determining the gas/oil ratio of the oil phase and the gas phase from separator 22 and knowing the amount of oil and gas supplied to the separator, the amount of the gas phase and oil phase in the separator at any given time can be readily calculated. This is necessary to assure that the capacity of the separator 22 is not exceeded.

Thus, there has been described specific embodiments for determining the phase behavior of oil/gas mixture at high pressures and temperatures. It will be understood by those skilled in the art that the above-described embodiments are merely exemplary and that it is susceptible to modification and variation without departing from the spirit and scope of the invention.

What is claimed is:

1. A method for determining the phase behavior of an oil/gas mixture at a predetermined temperature and pressure comprising:
    (a) separately feeding a flowing stream of pressurized oil and gas at a predetermined volume of oil and gas per unit time into a mixing chamber;
    (b) passing the effluent of mixed oil and gas from said mixing chamber into an oil-gas separator maintained at a predetermined absolute test pressure wherein the oil and gas separate by gravity;
    (c) surrounding said mixing chamber and said separator by a medium heated to a controlled, constant, elevated temperature;
    (d) withdrawing gas from the upper portion of said separator and continuously sensing the absolute pressure of said gas;
    (e) controlling the pressure of said gas within the separator in response to sensed pressure changes whereby said absolute pressure is maintained at a predetermined value;
    (f) withdrawing samples of oil from the bottom of said separator and measuring the content of gas in said oil; and
    (g) withdrawing samples of gas from the upper portion of said separator and measuring the content of oil in said gas.

2. The method of claim 1 wherein the absolute pressure of the gas withdrawn from the separator during step (d) is controlled within the range of 2,000 to 20,000 psi.

3. The method of claim 1 wherein the absolute pressure of the gas withdrawn from the separator during step (d) is controlled within the range of 8,000 to 15,000 psi.

4. The method of claim 1 wherein the temperature of the medium surrounding the mixing chamber and separator is controlled within the range of 100° F. to 600° F.

5. The method of claim 1 wherein the temperature of the medium surrounding the mixing chamber and separator is controlled within the range of 300° F. to 450° F.

6. The method of claim 1 wherein the flow rate of oil during step (a) is within the range of 0.5 cc/hr to 50 cc/hr and the flow rate of gas during step (a) is within the range of 50 to 300 liters/hr at standard temperature and pressure.

7. The method of claim 1 wherein the flow rate of oil during step (a) is within the range of 5 to 15 cc/hr and the flow rate of gas during step (a) is within the range of 100 to 200 liters/hr at standard temperature and pressure.

8. The method of claim 1 wherein said mixing chamber is filled with chips of silica.

9. The method of claim 1 wherein said heat medium surrounding the mixing chamber and separator is a constant temperature bath comprising a heated sand bath.

10. The method of claim 1 wherein said heat medium surrounding the mixing chamber and separator is a constant temperature bath comprising an oven.

11. The method of claim 1 wherein the residence time of the combined oil and gas stream in the mixing chamber is for a time period sufficient for thermo-dynamic equilibrium to be attained.

12. The method of claim 1 wherein said pressure control means comprises an elongated chamber having a first end and a second end opposite said first end; means for withdrawing gas from the upper portion of said separator, said means in fluid communication with said first end of said chamber; pressure responsive means longitudinally movable in sealing engagement with the internal walls of said chamber in fluid communication with both ends of said chamber; means for continuously supplying hydraulic fluid to said second end of said chamber for controlling the longitudinal movement of said pressure responsive means to provide a predetermined pressure in the first end of the chamber in fluid communication with said gas; means for sensing the absolute pressure within said second end of said chamber and control means responsive to said sensing means for controlling the pressure of said hydraulic fluid to a predetermined level.

13. The method of claim 12 wherein said pressure sensing means comprises a sensing element which is electrically responsive to pressure changes within the second end of said chamber and an electrical circuit interconnecting said sensing element and pressure control means whereby said absolute pressure of said gas is maintained at a predetermined level.

14. The method of claim 12 wherein the means for supplying said hydraulic fluid comprises a constant displacement pump.

15. The method of claim 12 wherein said hydraulic fluid is selected from the group consisting of mercury, oil and air.

16. The method of claim 13 wherein said sensing element comprises a pressure transducer.

17. Apparatus for determining the phase behavior of oil/gas mixtures comprising:
(a) means for constantly supplying a predetermined volume of pressurized oil and gas per unit time into a mixing chamber;
(b) an oil/gas separator positioned below said mixing vessel and in fluid communication therewith wherein the oil and gas separate by gravity;
(c) means for surrounding the mixing chamber and separator within a medium heated to a controlled, constant, elevated temperature;
(d) means for controlling the absolute pressure of said gas within the upper portion of said separator;
(e) means communicating with said separator at a bottom portion thereof for withdrawing an oil sample;
(f) means for measuring the amount of gas contained in the sample of oil withdrawn from the bottom portion of the separator;
(g) means communicating with said separator at an upper portion thereof for withdrawing a gas sample; and
(h) means for measuring the amount of oil contained in the sample of gas withdrawn from the upper portion of the separator.

18. The apparatus of claim 17 wherein said mixing chamber is tubing filled with inert chips of silica.

19. The apparatus of claim 17 wherein said means for controlling the absolute pressure of said gas within the upper portion of said separator comprises an elongated chamber having a first end and a second end opposite said first end; means for withdrawing gas from the upper portion of said separator, said means in fluid communication with said first end of said chamber; means longitudinally movable in sealing engagement with the internal walls of said chamber responsive to the pressure within both ends of said chamber; means for continuously supplying hydraulic fluid to said second end of said chamber for controlling the longitudinal movement of said pressure responsive means to provide a predetermined pressure in the first end of the chamber in fluid communication with said gas; means for sensing the absolute pressure within said second end of said chamber and means responsive to said sensing means for controlling the pressure of said hydraulic fluid to a predetermined level.

20. The apparatus of claim 19 wherein said means for sensing the absolute pressure within said second end of said chamber comprises a pressure transducer.

21. The apparatus of claim 19 wherein the means longitudinally movable in sealing engagement with the internal walls of said chamber comprises a piston.

22. The apparatus of claim 19 wherein the means for continuously supplying hydraulic fluid to said second end of said chamber comprises a constant displacement pump.

23. The apparatus of claim 19 wherein the means for continuously supplying hydraulic fluid to said second end of said chamber comprises a manually operated hydraulic press.

* * * * *